United States Patent [19]

Zini

[11] Patent Number: 5,203,720
[45] Date of Patent: Apr. 20, 1993

[54] MULTIPLE-CORE, MULTIPLE-SCREEN STRAP-TYPE CONNECTING CABLE, PARTICULARLY FOR ELECTROCARDIOGRAPHS OR FOR OTHER MEASURING INSTRUMENTS

[75] Inventor: Roberto Zini, Lugo di Ravenna, Italy

[73] Assignee: Mortara Rangoni Europe S.r.l., Italy

[21] Appl. No.: 772,925

[22] Filed: Oct. 8, 1991

[30] Foreign Application Priority Data

Oct. 10, 1990 [IT] Italy ............................... 15161/90[U]

[51] Int. Cl.$^5$ ............................................ H01R 13/00
[52] U.S. Cl. .................................................... 439/502
[58] Field of Search ................................. 439/502-506

[56] References Cited

U.S. PATENT DOCUMENTS

| | | | |
|---|---|---|---|
| 4,568,401 | 2/1986 | Davis | 439/502 |
| 4,799,899 | 1/1989 | Endo | 439/502 |
| 4,954,100 | 9/1990 | McCleerey | 439/502 |
| 4,954,101 | 9/1990 | Nelson | 439/502 |

Primary Examiner—Joseph H. McGlynn
Attorney, Agent, or Firm—Larson and Taylor

[57] ABSTRACT

A connecting cable uses a multiple-core, multiple-screen strap which is provided at one end with a terminal (6) within which are dischargers (12) for protection against excess voltages and with a connector (13) for removable connection to the electrocardiograph. At two intermediate points, with a suitable distance between them, the strap is provided with clamps (7-8) from which are branched separate leads for the peripheral and precodial branches. The leads are provided at their free ends with plugs (9) for connection to measuring electrodes, and electrical resistors for protection against excess voltages are preferably housed in the bodies of the plugs.

9 Claims, 2 Drawing Sheets

MULTIPLE-CORE, MULTIPLE-SCREEN STRAP-TYPE CONNECTING CABLE, PARTICULARLY FOR ELECTROCARDIOGRAPHS OR FOR OTHER MEASURING INSTRUMENTS

SUMMARY OF THE INVENTION

The connection of an electrocardiograph to the body of a patient is most commonly made at present through a multiple-core cable in which the various leads, electrically insulated from each other, are combined in a bundle and are surrounded by a number of concentric insulating sheaths and by a single screening braid. The cable has a connector at one end for removable connection to the instrument, and its other end is connected to a junction box in which metallic continuity must be provided between the various leads of the cable and said screen and the same number of single-core individually screened leads which have at their free end terminals for rapid and removable connection to the electrodes placed on the patient's body. Dischargers, normally of the gas type, are provided in the junction box for protection against excess voltages.

The electrical conductors and the sheaths forming the multiple-core cable and the single-core cables mentioned above are constructed from materials having considerable flexibility, high resistance to mechanical stresses and high technological reliability in general.

The present type of cable for electrical connection of an electrocardiograph to the patient's body has the disadvantage of a high production cost and presents problems of entanglement of the single-core leads emerging from the junction box, even if, in order to limit this disadvantage, use is made of special holders for grouping and for separating the leads for peripheral branches from those for precordial branches.

The invention proposes a connecting cable which is more economical, easier to use and more reliable than the conventional type described above. The new connecting cable uses a multiple-core, multiple-screen strap, permitting the total elimination of the aforesaid junction box. The dischargers are housed in the appropriate terminal, which permits removable connection of the new connecting cable to the electrocardiograph.

BRIEF DESCRIPTION OF THE DRAWINGS

The characteristics of the improved cable in question, and the advantages derived from it, will be evident from the following description which refers to the figures of the drawings, in which.

DESCRIPTION OF THE PREFERRED EMBODIMENTS

Figure 1:
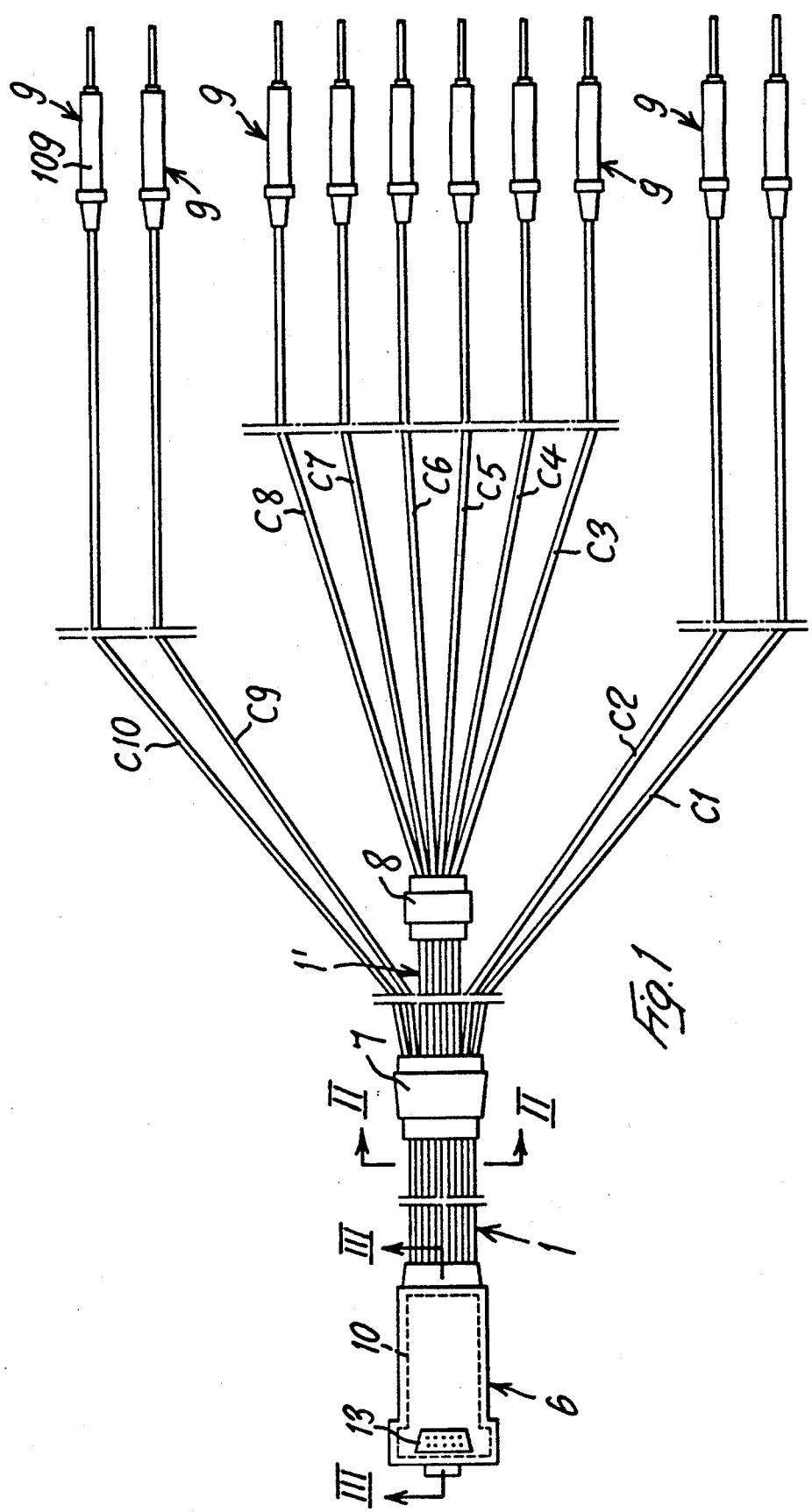
FIG. 1 is a schematic plan view of the new connecting cable.
Figure 2:
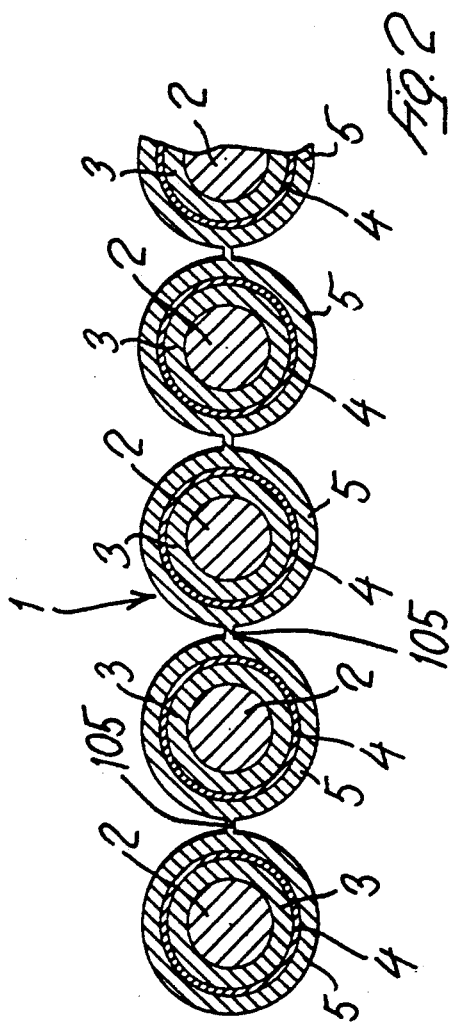
FIG. 2 shows a magnified partial view in transverse cross section taken along the line II—II in FIG. 1 of the multiple-core and multiple-screen strap forming the new connecting cable.

With reference to FIGS. 1 and 2 initially, it will be noted that the new connecting cable is provided with a number of electrical conductors 2 which are adjacent, flexible, parallel, and normally equidistant from each other, each of which is provided with at least one first flexible insulating sheath 3, then a flexible screening braid 4 and at least one flexible outer covering 5. The conductors, the screening and the insulating sheaths are made from any suitable materials having high technological reliability, such that they impart to the leads a considerable degree of flexibility and considerable resistance to mechanical stresses and to chemical and physical attack in general. The external sheaths 5 of the various leads are spaced a short distance apart, substantially in mutual contact, and are interconnected in a coplanar way by continuous webs 105 of suitable thickness. The webs 105 are made of the same material as that of the said sheaths, and the interconnections provided by webs 105 form a multiple-core strap 1, containing the desired number of individually screened leads. The strap 1, formed in this way, may be constructed by known methods of extrusion of the plastic material forming the sheaths 5 and the connections 105.

The new cable uses a section of multiple-core strap 1 of predetermined length, comprising for example 10 individually screened leads, which is provided at one end with a connector 6 described subsequently, for removable connection to the electrocardiograph. At the point at which branch connections to the electrodes for the upper and lower limbs of the patient are to branch off, the strap 1 is enclosed in a small flat body 7, having the function of a clamp, formed for example by injection of a suitable plastic material, preferably of the same type as that used in forming the sheaths 5. The leads for connection to the limbs are adjacent to each other and may be located on the same side of the strap or, as in the present example, on both sides of said strap. In the embodiment illustrated, the leads for connection to the limbs branching from the clamp 7, which are denoted C1-C2 and C9-C10 in FIG. 1, are mutually separated by breaking the web 105 connecting them together and to the other six leads C3 to C8 which form the section of strap 1' which extends outwardly from the clamp 7 and which remain interconnected.

At the point at which the individual connections for the precordial branches are to be taken off from the last section 1' of the strap (in other words at the branch point for the connections to the electrodes placed on the patient's chest), the strap is enclosed in a small flat body 8. Body 8 such the function of a clamp, and is also formed by injection of suitable plastic material. Leads C3 to C8 which are branched from the clamp 8 are separated from each other by breaking the interconnecting web 105, whose consistency is such that no substantial trace of the web remains, so as to provide maximum free sliding of the corresponding external sheath 5 of the individual leads.

The individual leads branched from the clamps 7 and 8 are cut to the necessary length and their free ends are connected to the plugs 9 for rapid and removable connection to the measurement electrodes attached to the patient's body. The connection to the plugs 9 is such that the necessary metallic continuity of the conductor 2 and of the screen 4 of each lead is ensured, and may include the connection of an electrical resistor of suitable value in series with each conductor, so as to limit the risk of excess voltages in the direction of the electrocardiograph, as employed, for example, in combined use with pacemakers, defibrillators or other electrical medical equipment. The body 109 of each plug 9, which covers the electrical connections to the lead and the aforesaid electrical resistor, is preferably formed by injection of a suitable plastic material (the same as used in the clamps 7 and 8), so as to prevent tampering with the plugs and to ensure a sealed connection between the sheath of the lead and the metal terminals of the plug.

It is to be understood that, in place of the coaxial plugs 9 shown in FIG. 1, it is possible to use other rapid and removable connecting devices, such as, for example, those of the snap fastener, crocodile, or other types.

Figure 3:
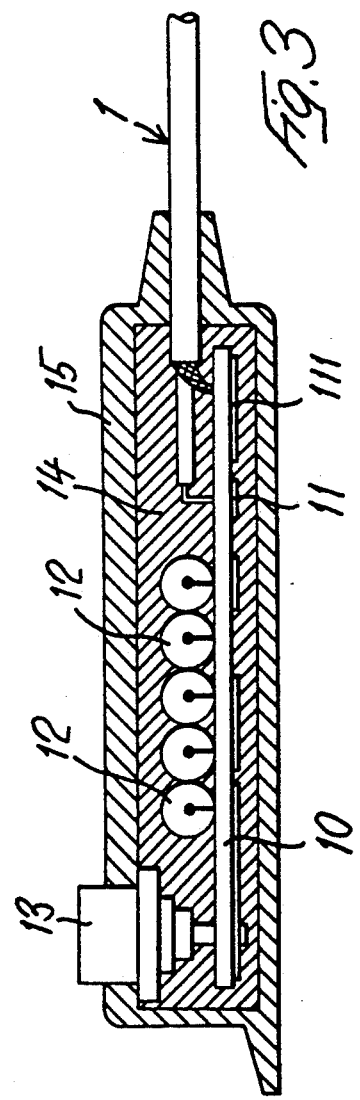
FIG. 3 shows the terminal for connecting the new cable to the electrocardiograph, in a longitudinal cross section taken along the line III—III in FIG. 1.

The composition of the terminal 6 for connection to the electrocardiograph will now be described, with reference to FIG. 3 as illustrated. This component comprises a printed-circuit base 10, provided at one end with points 11 for selective connection to the electrical conductors of the strap 1 and with one or more points 111 close to the points 11 and preferably outside thereof for connection to the screening 4 of the leads constituting the strap, which have previously been bundled together. The voltage dischargers 12 are mounted on the intermediate part of the base 10, and the multiple-core connector 13 to be inserted into the electrocardiograph socket is connected electrically and mechanically to the other end of the said base. The base 10, together with the components 12, and having previously been connected to the strap 1 and to the connector 13, is then placed in a small mould into which is injected epoxy resin 14 which rapidly solidifies and incorporates the parts described. These parts include an end section of the strap 1 and part of the body of the connector 13 which is thus securely fixed to the base. This may make it possible to carry out only the electrical connection of the connector to the base 10 beforehand.

The resin body 14 is then housed in another mould, into which is injected the same plastic material as that which forms the clamps 7 and 8, to provide the terminal 6 with a coating 15 of more suitable material. This ensures a sealed connection between the metal part of the connector 13 and the sheaths 5 of the leads forming the strap 1. Like the plugs 9, the terminal 6 cannot be tampered with.

It is to be understood that the terminal 6, with the connector 13, may have a shape in plan, which is different from the T shape illustrated in FIG. 1, and that the connector may be formed and oriented differently depending on the type of connection used in the electrocardiograph.

The simplicity of construction, the considerable economy and the considerable technological reliability of the connecting cable described should be evident from the foregoing, and are due to the continuity of the screening of the individual leads forming the strap, thereby permitting the elimination of the complex and expensive junction box used in known types of connecting cable. If appropriate terminals 9 and 13 are used, the new connecting cable is also completely sealed, a condition not present in known connecting cables, partly due to the internal accessibility of said junction box.

I claim:

1. A connecting cable for electrical instruments comprising a multiple-core strap formed by a plurality of single-core leads which are flexible and have substantially identical characteristics, each said leads being provided with a screen, and being disposed in a common plane adjacent to each other, in substantially mutual contact, said leads further being provided with an insulating sheath and being interconnected by at least one longitudinal continuous web made of the same material as that forming the external insulating sheath of the leads, said strap including, at one end thereof, a terminal with a connector for removable connection to a corresponding socket of an electrical instrument, said connector having incorporated therein protective means for providing protection for the electrical instrument, said strap including at first and second intermediate points therealong separate leads which branch off to form peripheral branches and precordial branches, and said strap further including at said first and second intermediate points first and second corresponding flat clamps which ensure that sections of said strap on the side of the said clamps closest to the electrical instrument remain in a fixed combined state, individual separate leads branching off from the clamps being cut to a required length and being connected with the free ends thereof to a corresponding connection means for providing rapid and removable connection to the measuring electrodes.

2. Connecting cable according to claim 1, wherein the at least one longitudinal continuous web is of such a consistency so as to be easily cut or torn thereby to permit the separation of said leads on the electrode side of the said clamps, and in such a manner that no substantial trace of said web remains on the separated leads, thereby to ensure free sliding of said separated leads.

3. Connecting cable according to claim 1, wherein individual leads for the peripheral branches which branch off from the first clamp are located on at least one side of said strap, so that the remainder of the strap remains whole and undivided up to the second clamp from which the individual leads for the precordial branches branch off.

4. Connecting cable according to claim 1, the clamps located at each branching of the individual leads from the strap are constructed so that the clamps enclose said strap in a body and are made of the same type of plastic material as that forming an outer covering of the strap.

5. Connecting cable according to claim 1, wherein said protective means comprises voltage dischargers.

6. Connecting cable according to claim 5, for use with an electrocardiograph wherein said terminal comprises a printed-circuit base on which are mounted the voltage dischargers and to which are electrically connected terminals of the individual leads of the strap and screening for the various leads, and to which are further connected an at least electrically connector for connection to the electrocardiograph, the connecting cable being enclosed in a block of self-hardening resin from which extends only a working terminal part of the connector, said block being provided with a covering of the same plastic material as that covering the strap.

7. Connecting cable according to claim 1, wherein said connection means comprises plugs.

8. Connecting cable according to claim 7, wherein the plugs located at the ends of the individual leads which branch off from the strap have bodies formed of plastic material of the same type as that of said clamps.

9. Connecting cable according to claim 7, wherein each lead is provided with an electrical resistor at a corresponding one of said plugs for protection against excess voltage.

* * * * *